United States Patent [19]

Engel et al.

[11] Patent Number: 5,935,310
[45] Date of Patent: Aug. 10, 1999

[54] INK FOR CHANGEABLE COLOR APPLICATIONS

[75] Inventors: Stefan Engel, Nürnberg; Anke Badewitz, Bayreuth, both of Germany

[73] Assignee: J.S. Staedtler GmbH & Co., Nürnberg, Germany

[21] Appl. No.: 09/088,313

[22] Filed: Jun. 1, 1998

[30] Foreign Application Priority Data

May 30, 1997 [DE] Germany ............... 197 22 546

[51] Int. Cl.⁶ .................................................. C09D 11/02
[52] U.S. Cl. ............................. 106/31.32; 106/31.42; 106/31.58; 106/31.28
[58] Field of Search ............... 106/31.32, 31.42, 106/31.58, 31.28

[56] References Cited

U.S. PATENT DOCUMENTS

| | | | |
|---|---|---|---|
| 2,305,098 | 12/1942 | Minnear | 106/31.32 |
| 4,179,397 | 12/1979 | Rohowetz et al. | 106/31.32 |
| 4,188,437 | 2/1980 | Rohowetz | 428/199 |
| 4,756,758 | 7/1988 | Lent et al. | 106/31.32 |
| 5,326,388 | 7/1994 | Miller et al. | 106/31.32 |
| 5,352,282 | 10/1994 | Miller | 106/31.32 |
| 5,486,228 | 1/1996 | Miller et al. | 106/31.32 |

FOREIGN PATENT DOCUMENTS

| | | |
|---|---|---|
| 27 24 820 | 12/1978 | Germany. |
| 08003494 | 6/1992 | Japan. |
| 94-140520 | 6/1994 | Japan. |

*Primary Examiner*—Helene Klemanski
*Attorney, Agent, or Firm*—Kenyon & Kenyon

[57] ABSTRACT

The present invention relates to an ink or India ink for variable ink applications, for writing, drawing, painting and printing, especially in connection with ink-jet systems or other mechanical writing, printing, painting or marking methods and/or devices, made up of organic solvent, as well as of a coloring agent and, optionally, water, binding agent and/or further additives. The coloring agent includes at least two chromophoric components, of which, in the print image, or after the stroke application or color application, at least one coloring-agent component is water-soluble, and a further coloring-agent component is water-insoluble. The components should include various colorants and/or color pigments, and should have at least one colorant that is water-soluble in the stroke application—especially under the influence of heat—and one water-insoluble colorant and/or one water-insoluble color pigment.

17 Claims, No Drawings

INK FOR CHANGEABLE COLOR APPLICATIONS

FIELD OF THE INVENTION

The present invention relates to an ink for changeable color, or "variable ink" applications. In particular, the present invention relates to ink for writing, drawing, painting and printing, especially in connection with ink-jet systems or other mechanical writing, printing, painting or marking methods or devices.

BACKGROUND INFORMATION

It should be understood that the term "inks", within the meaning of the present invention, also includes India inks of all types containing binding agent and/or pigments, in so far as they meet the stipulated requirements and fulfill the other conditions of the proposed embodiment.

Known from the German patent 27 24 820 B2 are "A Method and Working Means for Producing Colored Stroke Applications on a Document", whose color effect is changed by aftertreatment, after applying the ink on the document. According to that reference, the aftertreatment should be effected through chemical means with the assistance of a bleaching liquor, by which one of several colorants contained in the coloring agent is converted into its leuco form, so that only the other colorant then remains visible in its original color in the stroke application.

Thus, in that case, a color change in the stroke application is always effected on the basis of chemical reactions or changes within a coloring-agent component in the stroke application. If and to what extent color changes in the stroke application are also present or possible in that case, without any chemical aftertreatment and/or under temperature influences, is not discernible.

Moreover, also known are inks or India inks, in whose stroke applications a chemical reaction is triggered in response to exceeding a certain temperature, the reaction producing a color change in the stroke application. In those cases, the color change takes place because of a pH-value change of certain colorants having indicator effect. The disadvantage of such ink compositions is that special indicator colorants are needed, and that the color contrast before and after the color change is usually only very slight and poorly visible. Furthermore, the expenditure for producing such inks, which in part also act in a very corrosive manner, is high.

None of the known inks or India inks appears capable of clearly indicating specific treatment conditions or treatment methods of objects marked or labeled by them. In particular, it is not possible to indicate, for example, heating having been effected as part of a sterilization processes.

Therefore, an object of the present invention is to produce an ink or India ink for use in manual writing devices or in writing and drawing equipment, such as in continuous ink-jet equipment, which does not have the disadvantages mentioned, and whose stroke applications are capable of making known or indicating, without chemical means or aftertreatments, specific treatment conditions or treatment methods of objects marked or labeled by them.

SUMMARY OF THE INVENTION

The ink of the present invention has two different colorants, the one colorant being able to be washed out of the stroke application or the print image with water, for example hot water or with water vapor, and the other colorant being resistant to water, for example hot water. According to further developments of the inks or India inks of the present invention, optionally effected sterilization, preservation or other heating processes or their course can be indicated as well.

DETAILED DESCRIPTION

The proposed ink or India ink for variable ink applications is intended to be used for writing, drawing, painting and printing, especially in connection with ink-jet systems or other mechanical writing, printing, painting or marking methods and/or devices as well, and should be composed, in particular, of organic solvent (LM), as well as of a coloring agent (FM) that has two or more chromophoric components (FMK1, FMK2, . . . ), and, optionally, contains water (W), binding agent (BM) and/or other additives (Z1, Z2, Z3, Z4, . . . ).

According to the invention, the coloring agent (FM) should have at least two chromophoric components (FMK1, FMK2, . . . ), of which at least one coloring-agent component (FMK1; FS1) in the application or print image, that is to say, after the stroke application or ink application, is water-soluble and able to be washed out, and a further coloring-agent component (FMK2; FS2, FP) is water-insoluble, and thus durably fast during a treatment in the water bath or steam bath. In general, the terms "water-soluble" and "water-insoluble" as used herein refer to the ink after its application. Moreover, the term "water-soluble" should not be read to exclude inks or colorants that require some secondary condition, such as the application of elevated temperatures, in order to become water-soluble.

According to one special refinement, coloring agent (FM) should be made of various colorants (FS1, FS2, . . . ) and/or color pigments (FP), and have at least one colorant (FS1) that is water-soluble in the stroke application or in the print image, and one water-insoluble colorant (FS2) and/or a water-insoluble color pigment (FP).

If the ink is intended to be used for the indication of temperature treatments in a water bath or steam bath, this is carried out advantageously when the water-soluble colorant(s) (FS1) in the print image or stroke application, after the application, is or are only soluble under the simultaneous action of water and heat. To this end, the water-soluble colorant(s) (FS1) in the print image should or must, after the application and its drying, be soluble primarily in heated water or in water vapor.

In addition, for the production and long-term storage of the proposed ink or India ink, it is necessary that coloring agent (FM) altogether, or both color components (FS1;, FS2) in the ink mixture, i.e., before the application, is or are soluble in organic solvent (LM).

Although a multitude of suitable colorants are known, it has proven to be particularly advantageous if water-soluble colorant (FS1) is CI "Patentblau V", and water-insoluble colorant (FS2) is CI "Solvent Red 89". Alternatively, the water-insoluble coloring-agent component (FMK2) can also be a pigment (FP).

Optionally suitable as further colorants for the proposed use are also:

as water-soluble colorants (FS1): CI "Basic Blue 7" (CI=42595), CI "Basic Blue 11 (CI=44040), CI "Basic Red 1" (CI=45160); "Basic Violet 3" (CI=42555), "Basic Violet 10" (CI=42170), CI "Basic Violet 11:1" (CI=42174), CI "Solvent Red 35"; CI "Acid Red 87" (CI=45380), CI "Acid Orange 7" (CI=15510), CI "Acid Blue 9" (CI=42090), and/or CI "Acid Violet 58" (CI=16260).

On the other hand, as water-insoluble colorants (FS2), CI "Solvent Red 102" (CI 15675), CI "Solvent Red 125"; CI "Solvent Yellow 25", CI "Solvent Yellow 82", CI "Solvent Yellow 146", CI "Solvent Orange 56", CI Solvent Blue 25 (CI 74350), CI Solvent Blue 35 (CI 61554) and/or CI "Solvent Brown 52" can also be used. In this connection, however, care should always be taken that, in each case, sufficiently discernible color differences are present before and after the treatment.

The optionally used binding agent (BM) should be soluble in organic solvent (LM), but should be resistant to boiling water. Shellac and/or ketone resins have proven to be particularly suitable binding agents (BM) for this purpose.

Given the addition of water (W)—especially when used in ink-jet systems—it should be desalinated, or be a distillate or twice-distilled water.

As organic solvent (LM), above all ethanol, isopropanol, acetone or MEK (methyl ethyl ketone) have proven advantageous.

Depending on the application area and application method intended, further additives (Z . . . ), such as pH-regulators (Z1), conductivity agents (Z2), preserving agents (Z3), surfactants (Z4) and/or other additives can or should be admixed with the ink or India ink.

Preferably, in the acid range, acetic acid, or in the alkaline range, alkanolamines can be used as pH regulators (Z1), sodium lactate, lithium nitrate or potassium thiocyanate can be used as conductivity agents (Z2), and/or an isothiazolone derivative can be used as preserving agent (Z3). When the application area lies outside of the treatment of foods or similar application areas, if desired, a formaldehyde can also be used as preserving agent (Z3). Thus, the ink of the present invention is preferably an ink or India ink having organic solvents such as ethanol, isopropanol, acetone or MEK.

The ink or India ink is intended to be usable both in automatic writing equipment, such as in continuous-jet methods, and in conventional writing devices, and should indicate the treatment of objects imprinted with it, for example, within the framework of a sterilization process. When using the ink in manual writing devices, the use of a conductivity agent can be dispensed with, if desired.

Thus in general the ink according to this embodiment of the present invention has two different components or colorants, the one colorant being able to be washed out of the stroke application or the print image with hot water or with water vapor, and the other colorant being resistant to hot water.

When, for example, the water-soluble colorant is selected from CI "Food Blue 5" (=CI-No.: 42051) and the water-insoluble is selected from CI "Solvent Red 89", in response to action of water and heat that is sufficient timewise and temperature-wise, e.g. in the form of hot water vapor, a color change takes place from bluish violet to light red. The light red impression then indicates that the imprinted object was subjected to a corresponding treatment and, for example, is completely sterilized or adequately preserved. It can be understood that depending on the coloring agent and its amount used, the temperature level and the treatment duration can optionally be "set" in advance, so that the color change indicates concretely that the required treatment parameters are fulfilled. Also, if desired, the ethanol can be denatured with about 1% MEK.

Other colorants than those indicated by way of example are also possible. However, the selected colorants "Food Blue 5" and "Solvent Red 89" are particularly suitable, since given their use, both before and after a heating process under the influence of water, e.g. in a sterilization process in the steam bath or when boiling in highly heated water, a clear color contrast, or a definite color change can be recognized in the print image.

The stroke application or the print image must adhere well to the object to be marked, and all in all must be resistant to the treatment medium, e.g. to water vapor and/or hot water, over a certain period of time—at least until the sterilization process is completely finished. In addition, the imprint of such an ink or India ink should dry quickly at first, and should exhibit good adhesion on diverse backgrounds —also on relatively smooth surfaces.

In the following, the invention is explained more precisely with the aid of a framework formulation, as well as a few exemplary embodiments, wherein all percentages used herein (including within the claims) should be construed as approximations:

Framework formulation: (ink preparation/basic mixtures)

| | | |
|---|---|---|
| (LM) | organic solvent | 40 to 98% by weight |
| (FS1) | water-soluble colorant | 0.5 to 15% by weight |
| (FS2) | water-insoluble colorant/ pigment (FP) (FS2 / FP) | 0.5 to 10% by weight |
| (BM) | binding agent | 0.5 to 50% by weight |
| (W) | water | 0 to 40% by weight |
| (Z2) | conductivity agent | 0 to 15% by weight |
| (Z1) | pH-regulator | 0 to 15% by weight |
| (Z4) | surfactants | 0 to 5% by weight |
| (Z . . . ) | other additives (Z3, . . . ) | 0 to 15% by weight |

Exemplary embodiment 1: (finished ink)

| | | |
|---|---|---|
| (LM) | ethanol | 75.5% by weight |
| (W) | water | 3.4% by weight |
| (FS1) | CI Food Blue (CI-No.: 42051) | 1.9% by weight (water-soluble) |
| (FS2) | CI Solvent Red 89 | 3.5% by weight (water-insoluble) |
| (BM) | shellac | 13.2% by weight |
| (Z2) | sodium lactate | 2.5% by weight |

EXAMPLE 2: (finished ink)

| | | |
|---|---|---|
| (LM) | ethanol | 71.0% by weight |
| (W) | water | 12.5% by weight |
| (BM) | shellac | 9.0% by weight |
| (FS1) | CI Food Blue (CI-No.: 42051) | 1.5% by weight (water-soluble) |
| (FS2) | CI Solvent Red 89 | 2.0% by weight (water-insoluble) |
| (Z2) | sodium lactate | 2.5% by weight (50% in H2O) |
| (Z1) | acetic acid | 1.5% by weight (99–100%) |

What is claimed is:

1. An ink for color changeable applications, comprising:
   an organic solvent; and
   a coloring agent, the coloring agent including a first component and a second component, the first component including at least one water-soluble colorant and the second component including at least one of a water-insoluble colorant and a water-insoluble color pigment;
   wherein the at least one water-soluble colorant includes at least one of "Basic Blue 7", "Basic Blue 11", "Basic Red 1", "Basic Violet 3", "Basic Violet 10", "Basic Violet 11:1", "Solvent Red 35", "Acid Red 87", "Acid Orange 7", "Acid Blue 9", "Food Blue 5", and "Acid Violet 58"; and wherein the water-insoluble colorant includes at least one of "Solvent Red 102", "Solvent Red 125", "Solvent Red 89", "Solvent Yellow 25", "Solvent Yellow 82", "Solvent Yellow 146", "Solvent Orange 56", "Solvent Blue 25", "Solvent Blue 35", and "Solvent Brown 52".

2. The ink according to claim 1, wherein the at least one water-soluble colorant is soluble in water only after the application of elevated temperatures.

3. The ink according to claim 2, wherein the at least one water-soluble colorant is soluble only in one of hot water and heated water vapor.

4. The ink according to claim 1, wherein the first component and second component are each soluble in organic solvent.

5. The ink according to claim 1, wherein the second component is the water-insoluble color pigment.

6. The ink according to claim 1, further comprising a binding agent, the binding agent being soluble in organic solvent and resistant to boiling water.

7. The ink according to claim 6, wherein the binding agent is selected from the group consisting of a shellac and a ketone resin.

8. The ink according to claim 1, further comprising water, the water being selected from the group consisting of desalinated, distilled, and twice-distilled.

9. The ink according to claim 1, further comprising an organic solvent, the organic solvent being selected from the group consisting of ethanol, isopropanol, acetone, and Methyl ethyl ketone.

10. The ink according to claim 1, further comprising additional additives, the additional additives being selected from the group consisting of a pH regulator, a conductivity agent, a preserving agent, and a surfactant.

11. The ink according to claim 10, wherein said pH regulator is acetic acid.

12. The ink according to claim 10, wherein said pH regulator is alkanolamine.

13. The ink according to claim 10, wherein said conductivity agent is selected from the group consisting of sodium lactate, lithium nitrate, and potassium thiocyanate.

14. The ink according to claim 10, wherein said preserving agent is selected from the group consisting of formaldehyde and isothiazolone derivative.

15. The ink according to claim 1, wherein the ink includes:

40 to 98% by weight organic solvent;

0.5 to 15% by weight water soluble colorant;

0.5 to 10% by weight second component;

0.5 to 50% by weight binding agent;

0 to 40% by weight water;

0 to 15% by weight pH regulator;

0 to 15% by weight conductivity agent;

0 to 5% by weight surfactant; and 0 to 15% by weight other additives.

16. The ink according to claim 1, wherein the ink includes:

75.5% by weight organic solvent, the organic solvent being ethanol;

3.4% by weight water;

1.9% by weight "Food Blue 5";

3.5% by weight "Solvent Red 89";

13.2% by weight shellac; and 2.5% by weight sodium lactate.

17. The ink according to claim 1, wherein the ink includes:

71.0% by weight organic solvent, the organic solvent being ethanol;

12.5% by weight water;

9.0% by weight shellac;

1.5% by weight "Food Blue 5";

2.0% by weight "Solvent Red 89";

2.5% by weight sodium lactate; and 1.5% by weight acetic acid.

* * * * *